(12) United States Patent
Smithgall

(10) Patent No.: US 7,283,224 B1
(45) Date of Patent: Oct. 16, 2007

(54) FACE LIGHTING FOR EDGE LOCATION IN CATALYTIC CONVERTER INSPECTION

(75) Inventor: Brian Smithgall, Bozeman, MT (US)

(73) Assignee: Smithgall & Associates, Inc., Bozeman, MT (US)

( * ) Notice: Subject to any disclaimer, the term of this patent is extended or adjusted under 35 U.S.C. 154(b) by 172 days.

(21) Appl. No.: 10/955,428

(22) Filed: Sep. 30, 2004

(51) Int. Cl.
*G01N 21/00* (2006.01)

(52) U.S. Cl. ................... 356/237.1; 356/237.6

(58) Field of Classification Search ............ 356/237.1, 356/237.6, 602, 239.7, 237.2, 601; 250/559.45, 250/310
See application file for complete search history.

(56) References Cited

U.S. PATENT DOCUMENTS

| | | | |
|---|---|---|---|
| 5,548,400 A * | 8/1996 | Bourguinat | ............... 356/241.1 |
| 6,084,670 A | 7/2000 | Yamazaki et al. | |
| 2001/0028452 A1 | 10/2001 | Yoneda | |
| 2002/0105655 A1 * | 8/2002 | Svetkoff et al. | ............ 356/602 |
| 2003/0081202 A1 | 5/2003 | Yoneda | |
| 2003/0174320 A1 * | 9/2003 | Yokoyama et al. | ...... 356/237.6 |
| 2004/0217287 A1 * | 11/2004 | Watanabe et al. | ........... 250/310 |

* cited by examiner

*Primary Examiner*—Gregory J. Toatley, Jr.
*Assistant Examiner*—Tri Ton
(74) *Attorney, Agent, or Firm*—McKee, Voorhees & Sease, P.L.C.

(57) ABSTRACT

A method and system for inspecting an object having a planar face with surface variations such as catalytic converters. Light sources are placed above the planar face of the object for lighting the face of the object. At least one obscuration is positioned proximate the planar face of the object to limit the lighting of the planar face of the object to thereby provide a low depth field of lighting. The planar face of the object is imaged to provide an image representation of the planar face of the object. The image representation of the planar face of the object is evaluated to characterize edge chip damage.

13 Claims, 5 Drawing Sheets

FACE LIGHTING FOR EDGE LOCATION IN CATALYTIC CONVERTER INSPECTION

BACKGROUND OF THE INVENTION

The present invention relates to imaging technologies for inspection of devices such as, but not limited to, catalytic converters. More specifically, but not exclusively, the present invention relates to evaluating the presence or absence or edge chip damage for an object such as a catalytic converter. The problems in the art addressed by the present invention are described in terms of catalytic converters. The present invention, however, is not limited to catalytic converters, but can be used in other applications as well.

Catalytic converters are typically fragile ceramic blocks which can easily be damaged. Catalytic converters are comprised of a plurality of parallel tubes to form a honeycomb structured object. Due to the fragility of these ceramic blocks, the catalytic converters can be easily damaged particularly on the edges. This damage may be referred to as edge chips. These edge chips affect the performance and sealing of the catalytic converters into an enclosure. Thus, the presence of edge chips is a significant problem in catalytic converter manufacturing.

There is a need to provide for inspection of catalytic converters. Manufacturers of catalytic converter monoliths and diesel particulate filters (DPF) have been facing increasing demands from a customer base to perform 100 percent inspection of all product produced or processed in the plant. Such inspection would, of course, have to be of a nondestructive type. Therefore, it would be useful if imaging and image processing technologies could be used to improve the inspection process including evaluating for the presence of edge chips.

One of the problems with some inspection processes is their complexity. The complexity can include using multiple cameras, rotating objects or other cumbersome techniques. Therefore, it would be preferred if a practical, less cumbersome and less complex approach could be used.

In an inspection process, it would be preferred if only a single camera needed to be used and the object being inspected need not be rotated. Using multiple cameras to view edges from different angles by rotating the object would be more cumbersome and more complex.

BRIEF SUMMARY OF THE INVENTION

Therefore, it is a primary object, feature, or advantage of the present invention to improve upon the state of the art.

It is a further object, feature, or advantage of the present invention to provide for using imaging technologies to inspect objects such as catalytic converters for edge chips.

It is a still further object, feature, or advantage of the present invention to provide a method and system for inspecting catalytic converters that is practical and not cumbersome.

Another object, feature or advantage of the present invention is to evaluate an object for edge chips using only a single camera.

Yet another object, feature, or advantage of the present invention is to evaluate an object for edge chips as the object is moving during a manufacturing or production process.

A further object, feature, or advantage of the present invention is to provide a method for inspecting an object for edge chips that can be used to inspect 100 percent of all product produced or processed in a plant.

One or more of these and/or objects, features, or advantages of the present invention become apparent from the specification and claims that follow. The present invention is not to be limited by these objects or the Background of the Invention.

Accordingly, one aspect of the present invention a method for inspecting an object having a planar face with surface variations is disclosed. According to the method, light sources are provided above the planar face of the object for lighting the face of the object. At least one obscuration is positioned proximate the planar face of the object to limit the lighting of the planar face of the object. This configuration provides a low depth field of light. The planar face of the object is then imaged to generate an image representation of the planar face of the object. The image representation is evaluated in order to characterize edge chip damage. The object examined can be a honeycomb structured object such as a catalytic converter or other objects having a substantially planar face with surface variations. The camera used is preferably a line scan camera.

According to another aspect of the present invention a system for inspecting a honeycomb structured object to determine edge chip damage is disclosed. The system includes a camera positioned for imaging a face of the object and a plurality of light sources for lighting the face of the object. There is also a plurality of obscurations positioned proximate the face of the object to limit lighting of the face of the object to thereby provide a low depth field of lighting. The low depth field of lighting allows the imaging of the face of the object in a manner that reveals edge chip damage of the honeycomb structured object.

DETAILED DESCRIPTION OF THE PREFERRED EMBODIMENT

The present invention provides for a method and system for inspecting objects such as catalytic converts or other objects having a substantially planar face with surface variations that make detection of edge chips difficult using conventional approaches.

Figure 1:
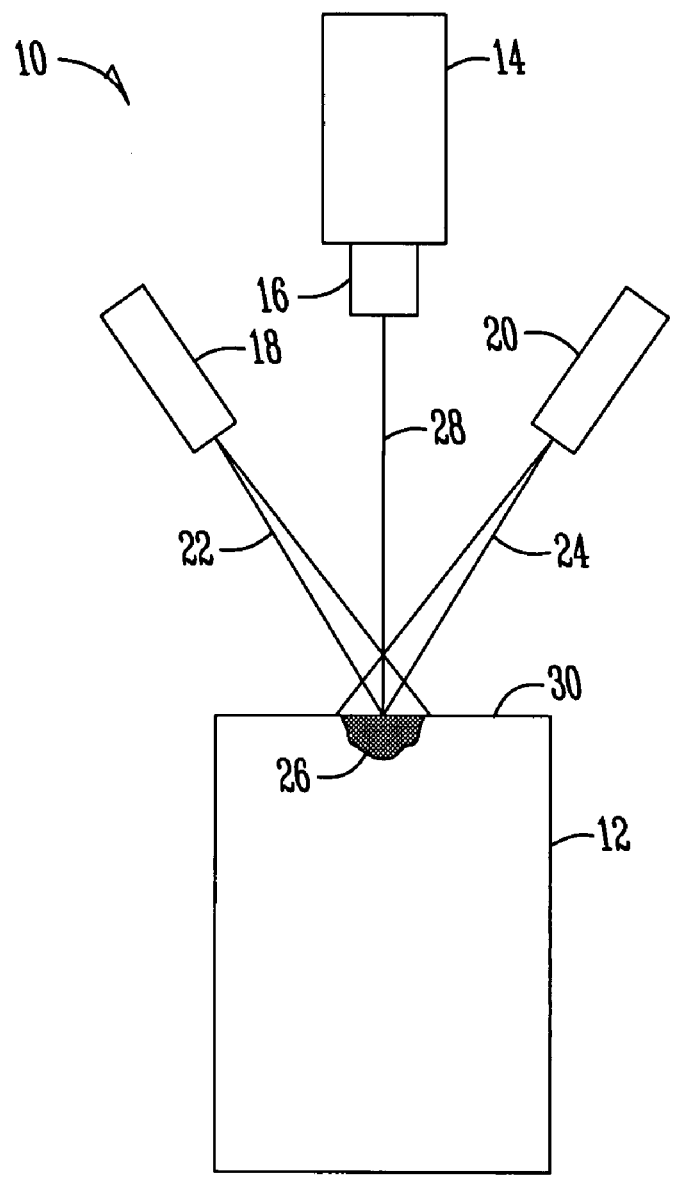
FIG. 1 is a block diagram of a prior art inspection system.

FIG. 1 illustrates a prior art system for inspecting an object such as a catalytic converter. In such a system, the object 12 is moving through a production process, such as on a conveyor belt or other mechanism. A camera 14 with a lens 16 looks downwardly on the face 30 of the object 12 as the object moves across the view of the camera 14. A line 28 indicates the optical axis between the camera 14 and the object 12. Light sources 18 and 20 are positioned on opposite sides of the camera 14. Both the light sources 18 and 20 are positioned at an angle relative to the optical axis 28. Light 22 and 24 is emitted from the light sources 18 and 20 to illuminate the planar surface 30 of the object 12. An edge chip or gouge 26 is shown in the object 12. The system 10 provides for normal lower linear lighting for a line scan camera imaging a moving part. The camera 14 images a narrow stripe across the object being inspected. The lighting only needs to illuminate a narrow stripe, although it could be lighting the entire part. Both of these narrow stripes are into the beam shown in FIG. 1. By the nature of the lighting, even though it is a narrow stripe, there is some beam divergence or width of lighting in the plane of the surface. The result is that if there is a gouge or chip at the edge of the object being inspection, the light gets into that part and the camera sees it as a normal edge. This is clear through examining the image of FIG. 2 which is of a catalytic converter with significant edge chips. The edge chips are not immediately apparent because there are what appears to be normal edges present because of light projecting into the object due to the properties of the object, including the surface variation.

Figure 3:
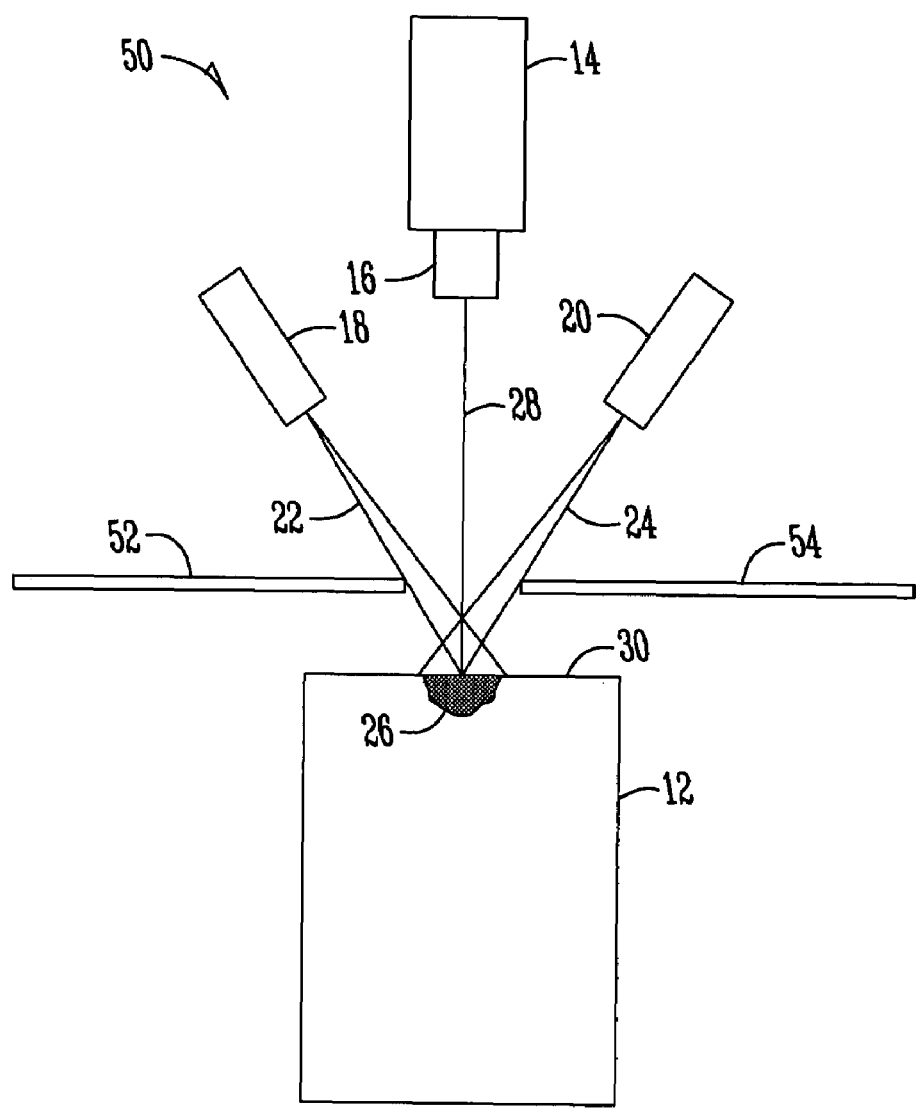
FIG. 3 is a block diagram of an inspection system of the present invention.

FIG. 3 illustrates the system 50 of the present invention. Note than in FIG. 3 that system 50 includes obscurations 52 and 54. Although two obscurations 52 and 54 are shown, the present invention contemplates that other numbers of obscuration could be used depending upon the particular application and context in which the invention is used. The observations need not be of any particular material or shape provided that they block the light. The purpose of the obscurations is to provide, in effect, a low depth of field lighting. Note that the lighting shown is one sided, from the inspection surface 30 up.

The precisely placed obscurations 52 and 54 limit the linear light cone to the one-sided lighting and the camera 14 images the face plane of the object 12. It is preferred that the light sources 18 and 20 are linear fiber lights. It is preferred that the line scan camera 14 has a standard lens 16. The obscurations 52 and 54 provide a straight edge to illuminate only the top surface of the part and not illuminate depressions, gouges or chips. Instead of providing one-sided lighting as shown, the present invention also contemplates that full area lighting with the same obscurations can be used.

Figure 2:
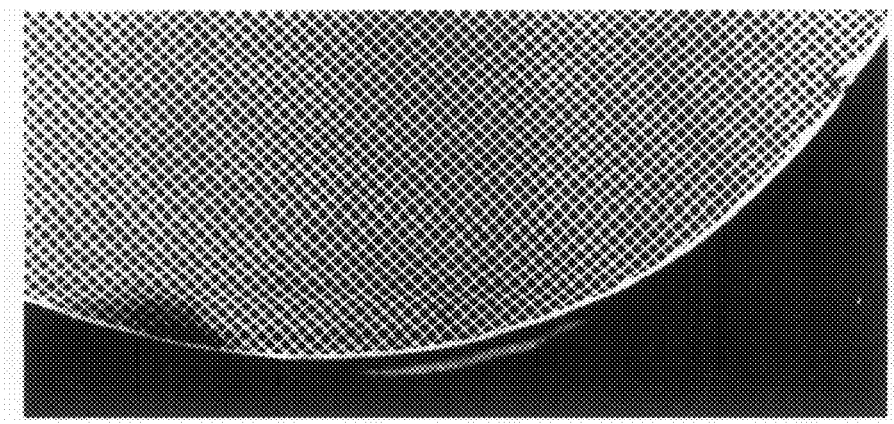
FIG. 2 is a photo of an image representation of a catalytic converter using the prior art system.
Figure 4:
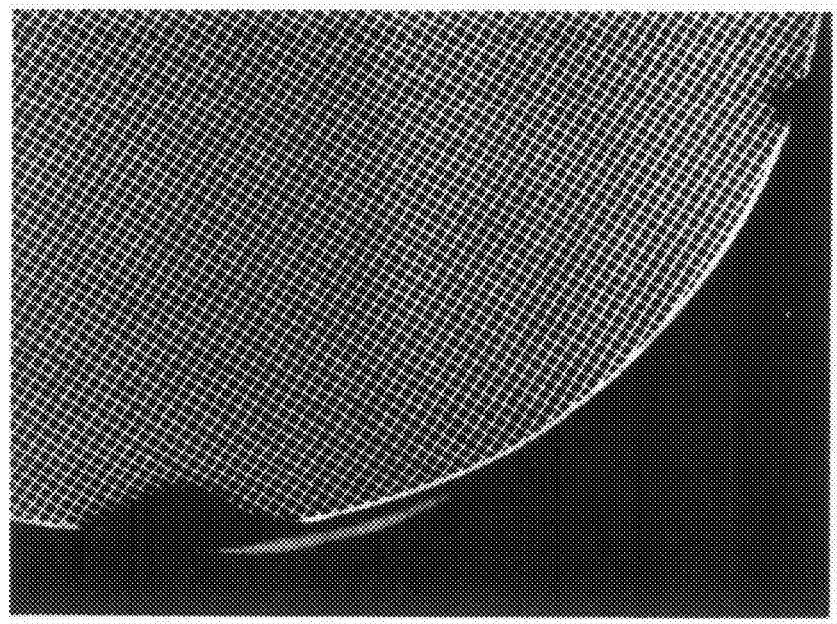
FIG. 4 is a photo of an image representation of a catalytic converter obtained using the inspection system of the present invention.

In a normal mode of application the line scan camera is vertical looking downward on the object to inspect. The lighting angle is as low as possible. That is to say that the lighting angle provides a steep angle to the vertical optical axis 28. It is observed that sometimes it is not practical to have the lighting more shallow than 45 degrees. Also, it may not necessarily be practical to have the lighting very close to the viewing point. The present invention recognizes that sometimes lenses can be used to narrow the light but even when such a lens is used, there is usually a somewhat wide beam. With the lighting sources 18 and 20 and camera 14 positioned as shown, the obscurations 52 and 54 should be placed in a plane parallel to and as close above the part as possible (for example 0.1 to 0.2 inches) so that the vast majority of the light on one side of the viewing point is blocked. The viewing stripe may be only a few thousandths of an inch wide, so blocking the light beyond this is appropriate. To set the position of the obscurations, the lights can be turned on one at a time, then the obscuration plane can be slid into place to just block the light and then it can be slid back to allow the lighting on the viewing area but not beyond that. Thus in this manner, the face of an object 12 can be evaluated to determine the presence of edge chips in the object. FIG. 4 is an image of a catalytic converter obtained according to the present invention. Compare FIG. 4 with FIG. 2. Note that the edge chips are more prominent in FIG. 4 such that edge chip damage is clearly shown. FIG. 2 and FIG. 4 are of the same catalytic converter. Once the images have been obtained, the images are processed for evaluation purposes. The objects can be characterized as having edge chips or not or by some measure of the extent of the edge chips. The image information may be processed in any number of ways using known image processing techniques or combinations of known image processing techniques.

The present invention contemplates that this aspect of the inspection process for the catalytic converter can be combined with other types of processes. For example, the present invention contemplates that this aspect of the inspection process can be combined with a method for detecting end cut perpendicularity as disclosed in U.S. patent application Ser. No. 10/873,942 herein incorporated by reference in its entirety. Thus, different methods of optical inspection can be combined for characterizing different properties of the object. For example, the present invention also contemplates that in addition to detecting edge chips, side defects can also be detected.

Figure 5:
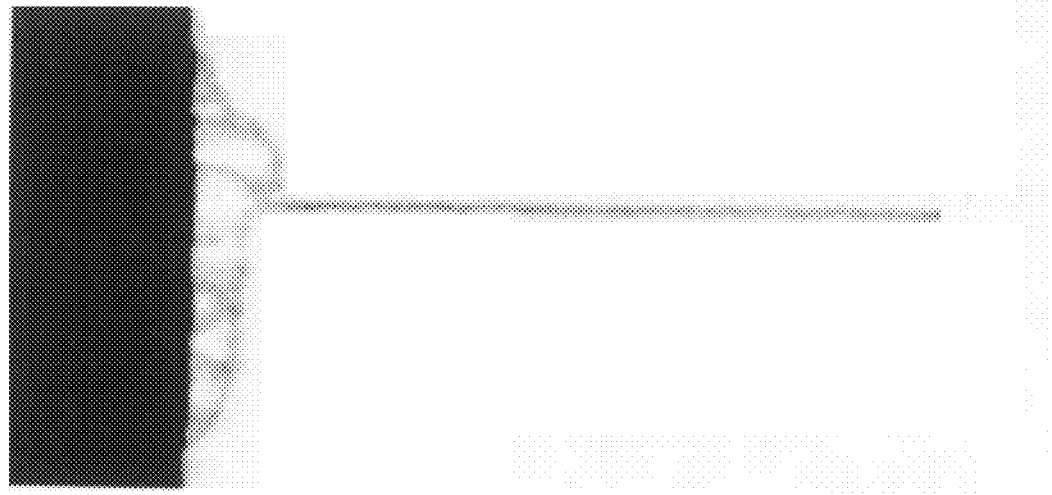
FIG. 5 is a photo of an image representation of a catalytic converter having a side crack with a small edge chip at the end of the side crack.

Side defects usually require the part to be rotated to image the entire surface from the side. If detailed detection is of interest, then a high resolution line scan camera can be used. As the part is rotated, the camera can be used for imaging the narrow stripe along the length of the surface. Sometimes there is a side crack associated with an edge chip. This is shown in the image of FIG. 5. By separately imaging for the side crack, the edge chip can be viewed from multiple perspectives which allows the extent of the edge chip to be better determined. Thus, the present invention contemplates combining the methodology for detecting and evaluating edge chips with one or more other methodologies used in inspecting a structure such as a catalytic converter to enhance the amount of information obtained concerning the edge chip but without increasing the overall number of views being needed.

Although a preferred embodiment has been set forth, the present invention is not limited to the preferred embodiment. The present invention contemplates numerous variations in terms of the specific structures, placement of the specific structures, specific steps used in the methodology, and other variations within the spirit and scope of the present invention. For example, the present invention contemplates that once images are acquired, numerous techniques can be used to process the image such as generally known in the art, including techniques for segmentation, matching, detection, classification and other techniques as may be appropriate in a particular context or particular application of the present invention.

What is claimed is:

1. A method for inspecting an object having a planar face with surface variations, comprising:
   providing light sources above the planar face of the object for lighting the face of the object;
   providing at least one obscuration positioned proximate the planar face of the object to limit the lighting of the planar face of the object to thereby provide a low depth field of lighting;
   imaging the planar face of the object to provide an image representation of the planar face of the object;
   evaluating the image representation of the planar face of the object to characterize edge chip damage;
   providing an output indicative of the edge chip damage; and
   acquiring an image representation associated with side cracks in the object and wherein the step of evaluating includes evaluating the image representation of the planar face of the object and the image representation associated with side cracks to characterize the edge chip damage.

2. The method of claim 1 wherein the object is a honeycomb structured object.

3. The method of claim 2 wherein the object is a catalytic converter.

4. The method of claim 1 wherein the step of imaging uses a line scan camera.

5. The method of claim 4 wherein the line scan camera includes a standard lens.

6. The method of claim 1 wherein the plurality of light sources is a first light source and a second light source, each of the first light source and the second light source having a lighting angle of less than 45 degrees with the planar surface.

7. The method of claim 6 wherein the first light source and the second light source are linear fiber lights.

8. A method for inspecting a honeycomb structured object having a planar face, comprising:
  providing a first light source and a second light source above the planar face of the object for lighting the planar face of the object;
  providing at least one obscuration positioned proximate the planar face of the object to limit the lighting of the planar face of the object to thereby provide a low depth field of lighting;
  imaging the planar face of the object with the scan camera with a standard lens to provide an image representation of the planar face of the object;
  acquiring an image representation associated with side cracks in the object;
  evaluating the image representation of the planar face of the object and the image representation associated with side cracks in the object to characterize edge chip damage of the object; and
  providing an output indicative of the edge chip damage of the object.

9. The method of claim 8 wherein the object is a catalytic converter.

10. The method of claim 8 wherein the first light source and the second light source are linear fiber lights.

11. A system for inspecting a honeycomb structured object to determine edge chip damage, comprising:
  a camera positioned for imaging a face of the object;
  a plurality of light sources for lighting the face of the object;
  a plurality of obscurations positioned proximate the face of the object to limit lighting of the face of the object to thereby provide a low depth field of lighting such that the imaging of the face of the object reveals edge chip damage of the honeycomb structured object;
  means for characterizing edge chip damage of the object based on the imaging of the face of the object and imaging of side cracks of the object.

12. The system of claim 11 wherein the honeycomb structured object is a catalytic converter.

13. The system of claim 11 wherein the camera is a line scan camera.

* * * * *